United States Patent
Stricker

(10) Patent No.: US 10,842,204 B2
(45) Date of Patent: Nov. 24, 2020

(54) RESISTANCE GARMENTS

(71) Applicant: Christian Andrew Stricker, Bend, OR (US)

(72) Inventor: Christian Andrew Stricker, Bend, OR (US)

( * ) Notice: Subject to any disclaimer, the term of this patent is extended or adjusted under 35 U.S.C. 154(b) by 23 days.

(21) Appl. No.: 16/270,779

(22) Filed: Feb. 8, 2019

(65) Prior Publication Data
US 2019/0239579 A1    Aug. 8, 2019

Related U.S. Application Data

(60) Provisional application No. 62/628,081, filed on Feb. 8, 2018.

(51) Int. Cl.
*A41D 13/00* (2006.01)
*A63B 21/04* (2006.01)
*A63B 21/055* (2006.01)
*A63B 21/00* (2006.01)
*A63B 23/04* (2006.01)
(Continued)

(52) U.S. Cl.
CPC .......... *A41D 13/0015* (2013.01); *A41D 1/089* (2018.01); *A41D 31/185* (2019.02); *A63B 21/0428* (2013.01); *A63B 21/0555* (2013.01); *A63B 21/4025* (2015.10); *A63B 23/0482* (2013.01); *A41D 2300/22* (2013.01); *A41D 2600/10* (2013.01)

(58) Field of Classification Search
CPC ...... A41D 13/0015; A63B 21/02–0557; A63B 21/065
See application file for complete search history.

(56) References Cited

U.S. PATENT DOCUMENTS

| | | | |
|---|---|---|---|
| 4,698,847 | A | 10/1987 | Yoshihara |
| 5,203,754 | A | 4/1993 | Maclean |
| 5,778,452 | A | 7/1998 | Dicker et al. |

(Continued)

FOREIGN PATENT DOCUMENTS

| | | |
|---|---|---|
| GB | 2501396 A | 4/2012 |
| JP | 2011168904 A | 2/2010 |

OTHER PUBLICATIONS

International Search Report and Written Opinion prepared by the US Receiving Office for PCT/US2019/017197, dated Apr. 30, 2019, 12 pages.

(Continued)

*Primary Examiner* — Jennifer Robertson
(74) *Attorney, Agent, or Firm* — Chernoff Vilhauer LLP

(57) ABSTRACT

Resistance garments are disclosed. In some embodiments, the resistance garments may include a body portion, first and second leg portions, and an elastic strap assembly secured to the body portion and the first and second leg portions. The elastic strap assembly may be configured to apply (1) a first force at the wearer's hips that urges the thighs of the wearer toward the wearer's torso, and (2) a second force at the wearer's thighs that urges the thighs of the wearer toward each other. In some embodiments, the elastic band assembly may include a belt, first and second knee bands, front elastic straps in the form of an X-shape with ends that are attached to, or formed with, the belt and knee bands, and rear elastic straps in the form of an X-shape with ends that are attached to, or formed with, the belt and knee bands.

17 Claims, 10 Drawing Sheets

(51) Int. Cl.
*A41D 1/089* (2018.01)
*A41D 31/18* (2019.01)

(56) References Cited

U.S. PATENT DOCUMENTS

| | | | |
|---|---|---|---|
| 5,857,947 A | 1/1999 | Dicker et al. | |
| 6,176,816 B1 | 1/2001 | Dicker et al. | |
| 7,559,093 B2 | 7/2009 | Sudo et al. | |
| 7,631,366 B2 | 12/2009 | Oyama et al. | |
| 7,730,552 B2 | 6/2010 | Ota et al. | |
| 7,814,576 B2 | 10/2010 | Nakazawa | |
| 7,945,970 B2 | 5/2011 | Belluye et al. | |
| 8,245,324 B2 | 8/2012 | Kawasaki et al. | |
| 8,578,514 B2 | 11/2013 | Caillibotte et al. | |
| 8,832,863 B2 | 9/2014 | Yang | |
| 8,850,619 B2 | 10/2014 | Rush et al. | |
| 9,095,177 B2 | 8/2015 | Ota et al. | |
| D774,731 S | 12/2016 | Harris et al. | |
| 10,039,330 B2 | 8/2018 | Tanaka et al. | |
| 10,051,897 B2 | 8/2018 | Freddi et al. | |
| 2011/0208104 A1 | 8/2011 | Sellier | |
| 2014/0207041 A1 | 7/2014 | Ingimundarson et al. | |
| 2015/0173993 A1* | 6/2015 | Walsh | B25J 9/0006 414/4 |
| 2015/0306441 A1* | 10/2015 | Yao | A63B 21/4019 482/124 |
| 2016/0339286 A1 | 11/2016 | Kehler et al. | |

OTHER PUBLICATIONS

CW-X Women's Expert Tights, retrieved from Running Warehouse website https://www.runningwarehouse.com/CW-X_Womens_Expert_Tight/descpage-CWWXT.html, Jan. 21, 2019.

McDavid Cross Compression Shorts, retrieved from Compressionsale.com, https://www.compressionsale.com/McDavid-Cross-Compression-Shorts.html?gclid=EAlaIQobChMIso_sZT_3wIVk7fACh0GYQcCEAkYECABEgJS-fD_BwE, Jan. 21, 2019.

* cited by examiner

RESISTANCE GARMENTS

CROSS-REFERENCE TO RELATED APPLICATIONS

This application claims the benefit of U.S. Provisional Patent Application Ser. No. 62/628,081, filed on Feb. 8, 2018 and entitled "Resistance Garments." The complete disclosure of the above application is hereby incorporated by reference for all purposes.

FIELD

This disclosure relates to clothing. More specifically, the disclosed embodiments relate to garments designed to enhance exercise and physical fitness.

INTRODUCTION

Gluteal amnesia is a condition in which a person cannot engage their gluteal muscles effectively. In many cases, gluteal amnesia is a consequence of routinely sitting for a large part of the day, which can lead to a tightening of the hip flexor muscle group and a corresponding lengthening of the gluteal group. Over time, the lengthened gluteal muscles lose the ability to activate (i.e., to contract in response to signals from the nervous system). Gluteal amnesia can reduce athletic performance in activities involving movement driven by the gluteal muscles and can lead to back pain caused by smaller muscles inappropriately compensating for the underperforming gluteal group.

To combat gluteal amnesia, many exercise regimens and physical therapy routines include gluteal activation. For example, an elastic resistance band may be worn around the knees during certain exercises. Performing these activities under the resistance provided by the band may cause the gluteal muscles to engage, countering the effects of gluteal amnesia. Wearing a resistance band around the knees could increase gluteal activation during a variety of workouts or even routine activities, such as walking, performing chores, or working in an office. However, the resistance band inhibits certain movements and may be unacceptable in appearance outside of a gym or other training environment. A device that provides the benefit of resistance bands around the knees without these drawbacks would afford many people the opportunity to improve their gluteal activation, leading to better physical performance and reduced back pain.

SUMMARY

The present disclosure provides systems, apparatuses, and methods relating to resistance garments to promote gluteal activation. In some embodiments, resistance garments may include a body portion configured to cover the pelvis of a wearer.

Resistance garments may additionally include first and second leg portions extending from the body portion, each sized to cover at least a portion of a thigh of the wearer. Resistance garments may further include an elastic strap assembly secured to the body portion and the first and second leg portions, the elastic strap assembly configured to apply (1) a first force at the wearer's hip that urges the thighs of the wearer toward the wearer's torso and (2) a second force at the wearer's thighs that urges the thighs of the wearer toward each other.

The elastic band assembly may include a belt sized to extend around the waist of the wearer. The belt may have front and rear portions. The elastic band assembly may additionally include first and second knee bands sized to extend around lower portions of the wearer's thighs at or above the wearer's knees. The first and second knee bands may each have front and rear portions. The elastic band assembly may further include front elastic straps in the form of an X-shape having a front central portion and first, second, third, and fourth ends. The first and second ends may be attached to, or formed with, the front portion of the belt. The third end may be attached to, or formed with, the front portion of the first knee band. The fourth end may be attached to, or formed with, the front portion of the second knee band. The elastic band assembly may additionally include rear elastic straps in the form of an X-shape having a rear central portion and fifth, sixth, seventh, and eighth ends. The fifth and sixth ends may be attached to, or formed with, the rear portion of the belt. The seventh end may be attached to, or formed with, the rear portion of the second knee band. The eighth end may be attached to, or formed with, the rear portion of the first knee band.

In some embodiments, resistance garments may include a body portion configured to cover the pelvis of a wearer. Resistance garments may additionally include first and second leg portions extending from the body portion, each sized to cover at least a portion of a thigh of the wearer. Resistance garments may further include means for applying (1) a first force at the wearer's hips that urges the thighs of the wearer toward the wearer's torso and (2) a second force at the wearer's thighs that urges the thighs of the wearer toward each other, the means for applying being secured to the body portion and the first and second leg portions.

In some embodiments, resistance garments may include a body portion configured to cover the pelvis of a wearer. Resistance garments may additionally include first and second leg portions extending from the body portion, each sized to cover at least a portion of a thigh of the wearer. Resistance garments may additionally include an elastic strap assembly secured to the body portion and the first and second leg portions, the elastic strap assembly configured to apply (1) a first force at the wearer's hip that urges the thighs of the wearer toward the wearer's torso and (2) a second force at the wearer's thighs that urges the thighs of the wearer toward each other.

The elastic band assembly may include a belt sized to extend around the waist of the wearer. The belt may have front and rear portions. The elastic band assembly may additionally include first and second knee bands sized to extend around lower portions of the wearer's thighs at or above the wearer's knees. The first and second knee bands may each have front and rear portions. The elastic band assembly may further include front elastic straps in the form of an X-shape having a front central portion and first, second, third, and fourth ends. The first and second ends may be attached to, or formed with, the front portion of the belt. The third end may be attached to, or formed with, the front portion of the first knee band. The fourth end may be attached to, or formed with, the front portion of the second knee band. The elastic band assembly may additionally include rear elastic straps in the form of an X-shape having a rear central portion and fifth, sixth, seventh, and eighth ends. The fifth and sixth ends may be attached to, or formed with, the rear portion of the belt. The seventh end may be attached to, or formed with, the rear portion of the second knee band. The eighth end may be attached to, or formed with, the rear portion of the first knee band.

The elastic band assembly may further include a first bridge elastic strap having opposed ninth and tenth ends. The ninth end may be attached to, or formed with, the front central portion and a portion of the front elastic straps between the front central portion and the third end. The tenth end may be attached to, or formed with, one of (i) the eighth end of the rear elastic straps and the rear portion of the first knee band or (ii) a portion of the rear elastic straps between the rear central portion and the eighth end. The elastic band assembly may additionally include a second bridge elastic strap having opposed eleventh and twelfth ends. The eleventh end may be attached to, or formed with, the front central portion and a portion of the front elastic straps between the front central portion and the fourth end. The twelfth end may be attached to, or formed with, one of (a) the seventh end of the rear elastic straps and rear portion of the second knee band or (b) a portion of the rear elastic straps between the rear central portion and the seventh end.

Features, functions, and advantages may be achieved independently in various embodiments of the present disclosure, or may be combined in yet other embodiments, further details of which can be seen with reference to the following description and drawings.

DESCRIPTION

Various aspects and examples of resistance garments are described below and illustrated in the associated drawings. Unless otherwise specified, a resistance garment and/or its various components may contain at least one of the structures, components, functionalities, and/or variations described, illustrated, and/or incorporated herein. Furthermore, unless specifically excluded, the process steps, structures, components, functionalities, and/or variations described, illustrated, and/or incorporated herein in connection with the present teachings may be included in other similar devices and methods, including being interchangeable between disclosed embodiments. The following description of various examples is merely illustrative in nature and is in no way intended to limit the disclosure, its application, or uses. Additionally, the advantages provided by the examples and embodiments described below are illustrative in nature and not all examples and embodiments provide the same advantages or the same degree of advantages.

Overview

In general, a resistance garment is configured to provide a tension or force that tends to oppose movement of a muscle group, such that moving while wearing the garment increases engagement of that muscle group. For example, a resistance garment may provide a force that tends to move the wearer's thighs toward each other, such that countering the force causes the wearer to engage their gluteal muscles. Additionally, or alternatively, the resistance garment may provide a force that urges the thighs of the wearer toward the wearer's torso. The tension may be provided by elastic portions of the garment, e.g., elastic bands, panels, or cords. In some embodiments, the garment is also a compression garment, configured to fit tightly (e.g., skintight) and supportively on the body. The garment may also be suitable for use as an ordinary piece of clothing that covers a portion of the body and protects it from the elements.

EXAMPLES, COMPONENTS, AND ALTERNATIVES

The following sections describe selected aspects of illustrative resistance garments as well as related systems and/or methods. The examples in these sections are intended for illustration and should not be interpreted as limiting the entire scope of the present disclosure. Each section may include one or more distinct embodiments or examples, and/or contextual or related information, function, and/or structure.

A. ILLUSTRATIVE RESISTANCE TIGHTS INCLUDING FIRST ILLUSTRATIVE TENSION BAND ASSEMBLY

Figure 1:
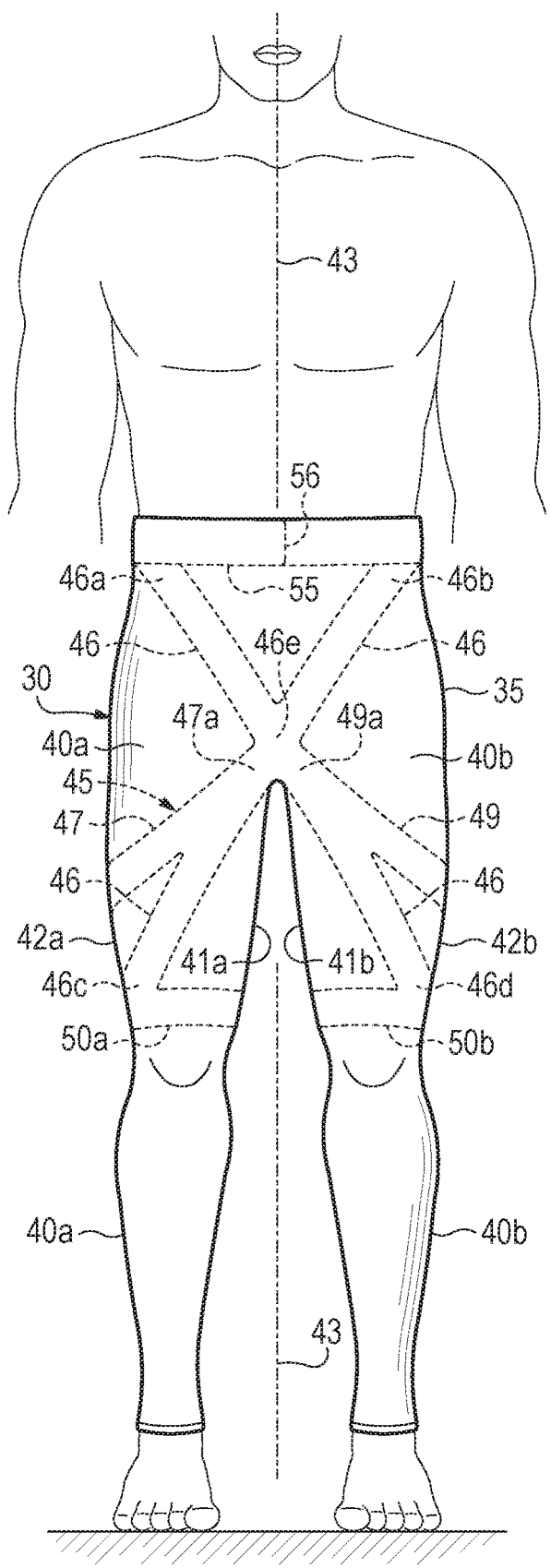
FIG. 1 is a front view of an illustrative example of a resistance garment, in accordance with aspects of the present disclosure.
Figure 2:
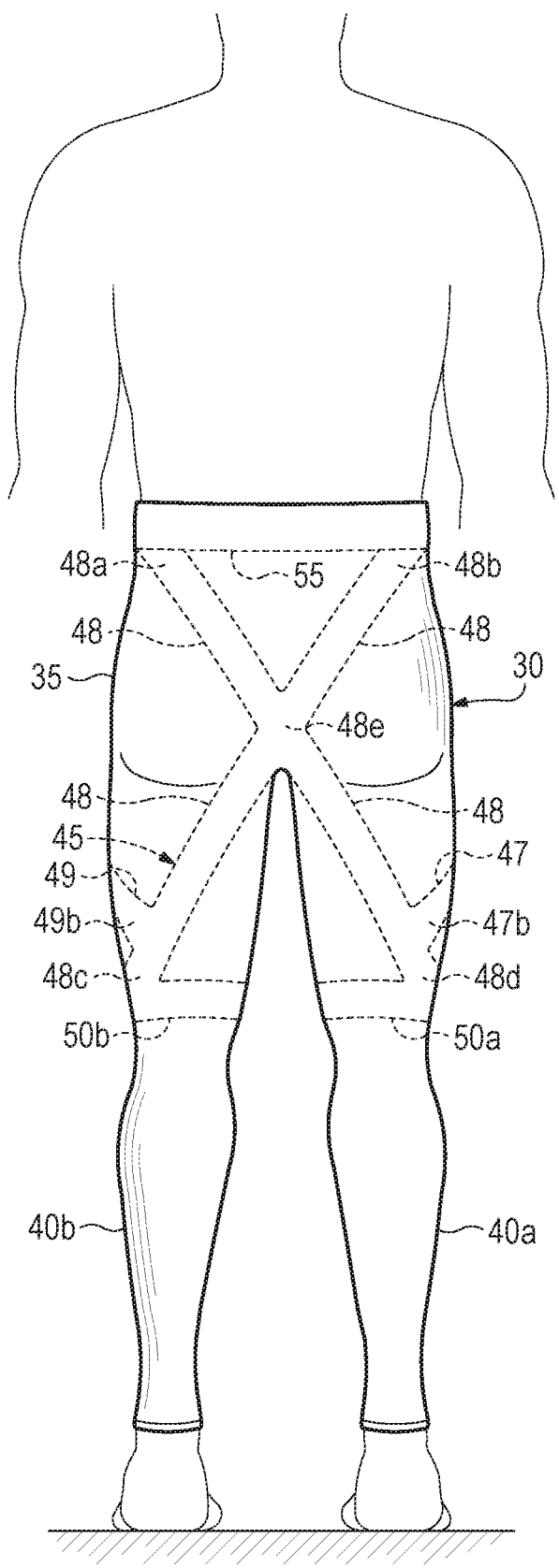
FIG. 2 is a back view of the resistance garment of FIG. 1.
Figure 3:
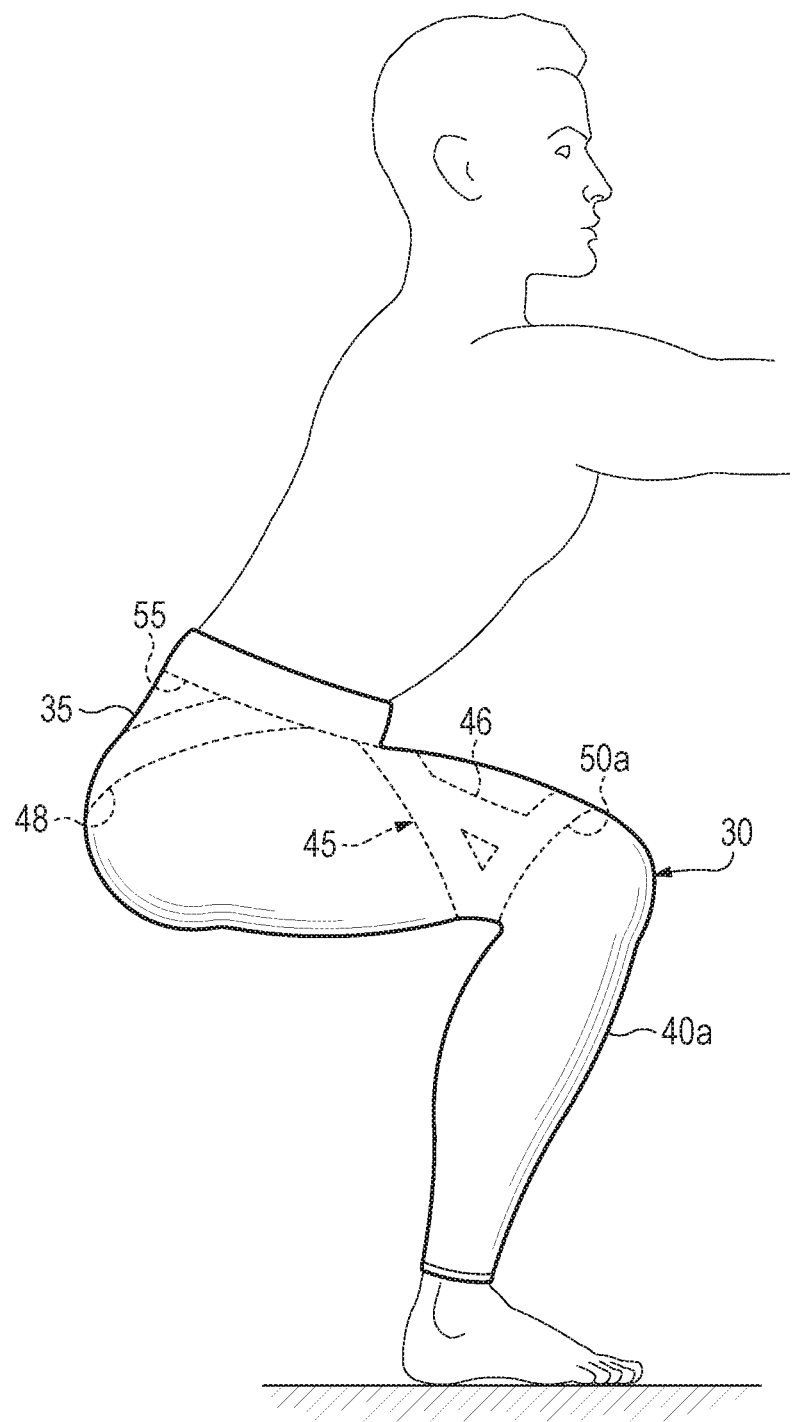
FIG. 3 is a side view of the resistance garment of FIG. 1, shown with the wearer performing a squat.

This section describes illustrative resistance tights 30, depicted in FIGS. 1-3. Resistance tights 30, which may also be referred to as resistance leggings, resistance pants, or a resistance leotard, are an example of a resistance garment, described above.

FIG. 1 is a front view of an illustrative pair of resistance tights 30. Resistance tights 30 include a body portion 35 connected to two leg portions 40a, 40b. Body portion 35 and leg portions 40a, 40b may each be formed by one or more pieces and/or panels of fabric. Body portion 35 covers at least a portion of the wearer's pelvis and may extend to cover a portion of the abdomen. Leg portions 40a, 40b extend from body portion 35 to cover a portion of the wearer's legs. Unless explicitly described otherwise, "leg" refers to the entire lower limb of the wearer, including the wearer's hip and gluteal region. In some embodiments, leg portions 40a, 40b extend to the knees of the wearer. In other embodiments, leg portions 40a, 40b extend past the knees (e.g., to the ankles or beyond the ankles, such as shown in the example of FIGS. 1-3) or extend only to a middle or upper region of the thighs. Leg portions 40a, 40b have respective inner sides 41a, 41b and outer sides 42a, 42b. Inner sides 41a, 41b are regions of leg portions 40a, 40b near an imaginary axis 43 running vertically through the center of the wearer's body. Outer sides 42a, 42b are regions of leg portions 40a, 40b distal axis 43 (i.e., opposite respective inner sides 41a, 41b).

Resistance tights 30 include an elastic strap assembly or tension band assembly 45 configured to urge the wearer's knees and/or thighs inward toward each other, and/or to urge the thighs of the wearer toward the wearer's torso. Tension band assembly 45 may include elastic bands, cords, or panels integrated into resistance tights 30. In some embodiments, tension band assembly 45 is attached to an inside surface of resistance tights 30 (i.e., against the wearer's skin) or to an outside surface of the tights (i.e., separated from the wearer's skin by fabric). In other embodiments, tension band assembly 45 is disposed between layers of fabric or inside pockets of fabric in resistance tights 30. Tension band assembly 45 may be attached to the fabric of resistance tights 30 by stitches, adhesive, or any other suitable means. In some embodiments, tension band assembly 45 is formed by portions of the fabric of resistance tights 30 having greater tension than the adjacent fabric; i.e., the tension band assembly may be woven, knit, or otherwise integrated into the fabric of the resistance tights. Integrating tension band assembly 45 into the fabric of resistance tights 30 eliminates stitches, seams, and/or other discontinuities that would otherwise occur in the tights and possibly cause discomfort to the wearer. The integrated tension band assembly 45 may have a different color and/or texture from the adjacent fabric. The distinct color and/or texture may enhance the wearer's proprioception and awareness of the effect of tension band assembly 45 on their movement and may add aesthetic appeal.

FIGS. 1-3 depict a first illustrative embodiment of tension band assembly 45 in resistance tights 30. In this embodiment, tension band assembly 45 includes front straps 46 and rear straps 48. Front straps or front elastic straps 46 may be in the form of any suitable shape(s). For example, front straps 46 may be in the form of an X-shape as shown in FIG. 1. Front straps 46 may include a first end 46a, a second end 46b, a third end 46c, a fourth end 46d, and a front central portion 46e. The first and fourth ends are opposed, while the second and third ends are opposed. The width of front straps 46 may be consistent or may be greater at leg portions 40a, 40b (such as between the front central portion and the third and fourth ends) than at body portion 35 (such as between the first and second ends and the front central portion), or vice-versa. In the example shown in FIGS. 1-3, tension band assembly 45 also may be described as having two intersecting front straps 46. Although front straps 46 are in the form of an X-shape, the front straps may be in the form of other shape(s), such as Y-shape, V-shape, U-shape, etc.

The elasticity of front straps 46 tends to pull the wearer's legs toward each other (i.e., inward). For example, the front straps apply a force at the wearer's thighs that urges the thighs of wearer toward each other. Additionally, the elasticity of front straps 46 tends to pull the wearer's torso toward the wearer's legs such that the wearer's hips flex. For example, the front straps apply a force at the wearer's hips that urges the thighs of the wearer toward the wearer's torso. A wearer of resistance tights 30 tends to engage their gluteal muscles to counter the tension provided by front straps 46 (or other embodiments of tension band assembly 45). Additionally, moving while wearing resistance tights 30 can increase the wearer's sense of where their gluteal muscles are located (i.e., the wearer's proprioception) and whether their gluteal muscles are engaging.

In the example shown in FIGS. 1-3, resistance tights 30 include knee bands 50a, 50b extending around at least a portion of the respective circumference of leg portions 40a, 40b at or near (e.g., above) the wearer's knees. Knee bands 50a, 50b may be elastic and may be part of tension band assembly 45. They may attach to front straps 46. In the example shown in FIGS. 1-3, knee bands 50a and 50b and front straps 46 are formed by a single piece of material. In other words, third end 46c and fourth end 46d are formed with front portions of knee bands 50a and 50b, respectively (front portions being the portions adjacent to or over the front of the knees of the wearer). However, the front straps may alternatively be attached to the knee bands. The third and fourth ends may be attached to any suitable portions of the knee bands. Although third end 46c and fourth end 46d are shown to be attached to, or formed with, portions of the knee bands that are adjacent to outer sides 42a and 42b, one or both of those ends may be attached to, or formed with, portions of the knee bands that are adjacent inner sides 41a and 41b (or that are disposed between the outer sides and the inner sides).

Knee bands 50a, 50b may help to keep resistance tights 30 in place on the wearer's body. For example, they may keep resistance tights 30 from being pulled up the wearer's legs by the tension of front straps 46 or other components of tension band assembly 45. In some embodiments, knee bands 50a, 50b are disposed at the middle or upper regions of the wearer's thigh rather than near the knee. Leg portions 40a, 40b may terminate at knee bands 50a, 50b, or may extend beyond the knee bands.

In the example shown in FIGS. 1-3, resistance tights 30 includes a belt 55 at or adjacent the top of body portion 35. Belt 55 may be elastic and may be part of tension band assembly 45. Belt 55 may attach to, or be formed with, front straps 46 and/or other components of tension band assembly 45. In some embodiments, belt 55 and front straps 46 are formed by a single piece of material. For example, first end 46a and second end 46b may be attached to, or formed with, opposed end portions of a front portion of belt 55, as shown in FIG. 1. The front portion of the belt being the portion that is adjacent to or over the front portion of the wearer's waist. Although first end 46a and second end 46b are shown to be attached to, or formed with, opposed end portions of the front portion of the belt, the first and second end may be attached to other suitable portions of the belt (such as between end portions of the front portion and a central portion of the front portion).

Figure 10:
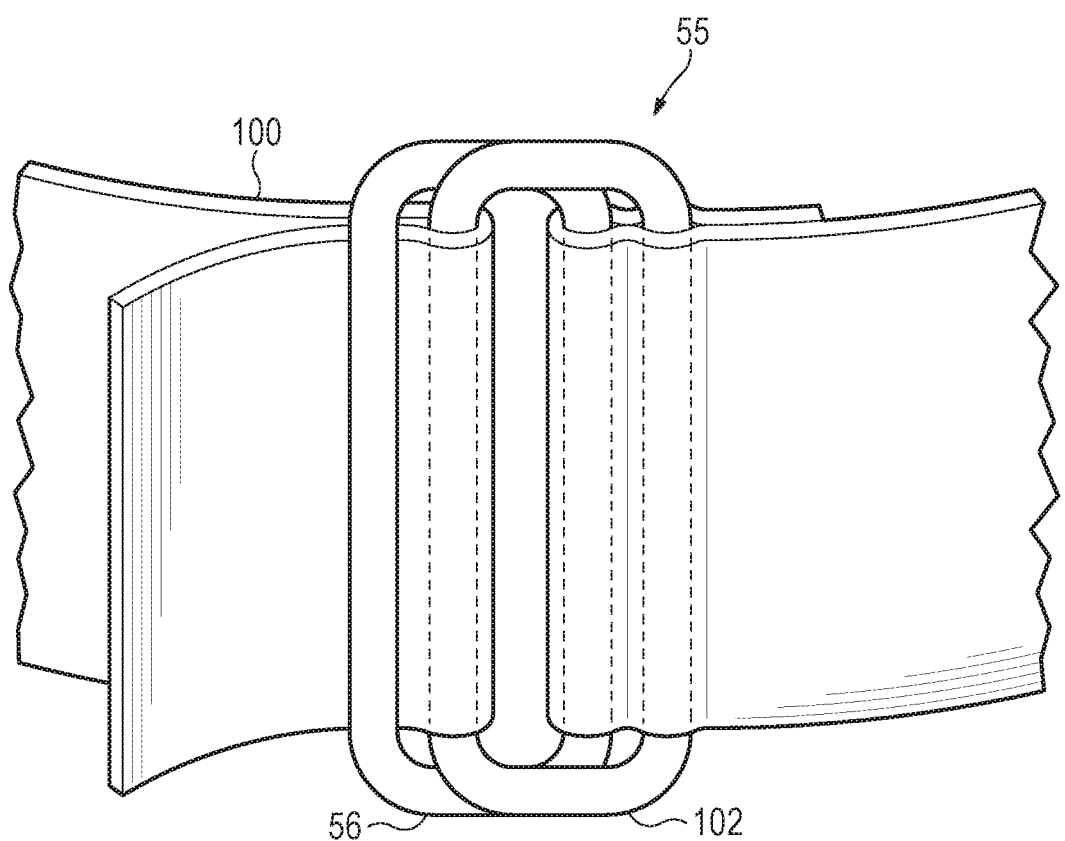
FIG. 10 is a partial view of a resistance garment of the present disclosure showing an illustrative example of a belt.

Belt 55 may include a tightening mechanism 56 configured to selectively adjust the tension or circumference of the belt. The tightening mechanism may include one or more buckles, buttons, snaps, drawstrings, Velcro material, or any other mechanisms suitable for adjusting the length/circumference or tightness of belt 55. For example, FIG. 10 shows an example of a belt 55 having a strap 100 and a tightening mechanism 56 in the form of a buckle 102. The strap may be attached to the body portion except for end portions of the strap to allow for adjusting the circumference via the tightening mechanism. In other embodiments, belt 55 may be without a tightening mechanism, such as an elastic strap sized to extend around the waist of a wearer. Belt 55 may help to keep resistance tights 30 in place on the wearer's body. For example, it may keep resistance tights 30 from being pulled down the wearer's legs by the tension of front straps 46 and/or other components of tension band assembly 45.

FIG. 2 depicts a back view of illustrative resistance tights 30. In the embodiment illustrated in FIG. 2, tension band assembly 45 includes rear straps or rear elastic straps 48. Rear straps 48 may be in the form of any suitable shape(s). For example, rear straps 48 may be in the form of an X-shape as shown in FIG. 2. Rear straps 48 may include a fifth end 48a, a sixth end 48b, a seventh end 48c, an eighth end 48d, and a rear central portion 48e. The fifth and eighth ends are opposed, while the sixth and seventh ends are opposed. The width of rear straps 48 may be consistent or may be greater at leg portions 40a, 40b (such as between the front central portion and the third and fourth ends) than at body portion 35 (such as between the first and second ends and the front central portion), or vice-versa. Tension band assembly 45 also may be described as include two intersecting rear straps. Although rear straps 48 are in the form of an X-shape, the rear straps may instead be in the form of a Y-shape, U-shape, V-shape, etc.

Rear straps 48 may be attached to front straps 46 and/or knee bands 50a, 50b, and may be formed by the same piece of material as the front straps and/or knee bands. Rear straps 48 may attach to belt 55. In some embodiments, rear straps 48 and/or front straps 46 are formed by the same piece of material as belt 55 and/or the knee bands. For example, fifth end 48a and sixth end 48b may be attached to, or formed with, a rear portion of belt 55, seventh end 48c may be attached to, or formed with, a rear portion of knee band 50b, and eighth end 48d may be attached to, or formed with, a rear portion of knee band 50a, as shown in FIG. 2. The rear portion of belt 55 being the portion that is adjacent to (or over) the back of the wearer, while the rear portion of the knee bands being the portion that is adjacent to (or over) the back of the knees of the wearer.

Fifth end 48a and sixth end 48b may be attached to, or formed with, any suitable portions of the belt. Although fifth end 48a and sixth end 48b are shown to be attached to, or formed with, opposed end portions of the rear portion of the belt, the fifth and sixth end may be attached to other suitable portions of the belt (such as between end portions of the rear portion and a central portion of the rear portion). Additionally, the seventh and eighth ends may be attached to any suitable portions of the knee bands. Although seventh end 48c and eighth end 48d are shown to be attached to, or formed with, portions of the knee bands that are adjacent to outer sides 42a and 42b, one or both of those ends may be attached to, or formed with, portions of the knee bands that are adjacent inner sides 41a and 41b (or that are disposed between the outer sides and the inner sides). Rear straps 48 provide a force tending to draw the wearer's legs and/or knees toward each other. Additionally, rear straps 48 may extend across the wearer's gluteal muscle group and thereby aid in the wearer's perception of where the gluteal muscles are positioned.

Tension band assembly 45 may include any suitable number of bridge straps that connect front straps 46 and rear straps 48 at any suitable locations. In the example shown in FIGS. 1-3, tension band assembly 45 includes first bridge strap 47 and second bridge strap 49. For example, first bridge strap 47 may include a ninth end 47a that is attached to, or formed with, a portion of front straps 46 between front central portion 46e and third end 46c. First bridge strap 47 also may include a tenth end 47b opposed from ninth end 47a that is attached to, or formed with, eighth end 48d of the rear straps. Additionally, second bridge strap 49 may include an eleventh end 49a that is attached to, or formed with, a portion of front straps 46 between front central portion 46e and fourth end 46d. Second bridge strap 49 also may include a twelfth end 49b that is attached to, or formed with, seventh end 48c of the rear straps. The bridge straps also may be attached to, or formed with, the front central portion of the front straps and the rear portion of the knee bands. For example, ninth end 47a of first bridge strap 47 and eleventh end 49a of second bridge strap 49 may be attached to, or formed with, opposed ends of front central portion 46e. Additionally, tenth end 47b of first bridge strap 47 may be attached to, or formed with, the rear portion of knee band 50a, and twelfth end 49b of second bridge strap 49 may be attached to, or formed with, the rear portion of knee band 50b. When included with tension band assembly 45, the bridge straps may spread tension from front straps over a region of outer sides 42a, 42b, reducing the likelihood of pain or injury to the wearer's legs. Although the example shown in FIGS. 1-3 include only first and second bridge straps 47 and 49, other examples of the tension band assembly may exclude the first and/or second bridge straps and/or may include other bridge straps.

FIG. 3 depicts a side view of resistance tights 30 on a wearer performing a squat. Front straps 46 tend to pull the wearer's upper body forward toward their thighs. The elasticity and/or tension of rear straps 48 may be less than the elasticity and/or tension of front straps 46, so that the tendency of the rear straps to pull the wearer's hips open (i.e., to pull the legs away from the torso) does not impede the tendency of the front straps to pull the hips closed (i.e., to pull the legs toward the torso).

Resistance tights 30 may be made of one or more types of woven or knit fabric. Typically, resistance tights 30 are made of an elastic or springy fabric that conforms to the wearer's body (e.g., skintight). The fabric may be configured to be moisture-wicking or to have a high degree of protection from sunlight (i.e., a high sun protection factor SPF or ultraviolet protection factor UPF). In some embodiments, the fabric of resistance tights 30 is substantially opaque, such that the tights are suitable for outerwear. In such embodiments, resistance tights 30 may function as running tights or leggings. Resistance tights 30 may fit tightly to compress the legs and/or body of the user, functioning as compression sportswear.

The amount of force applied on the legs and/or body of the wearer by tension band assembly 45 depends on the extent to which the elastic bands of the tension band assembly are stretched. In some embodiments, tension band assembly 45 is configured to apply a force corresponding to a weight of at least 1 kilogram to the wearer's knees during typical wear. In some embodiments, tension band assembly 45 is configured to apply a force corresponding to 1-3 kilograms during typical wear. In other embodiments, tension band assembly 45 is configured to apply a force corresponding to 3-5 kilograms during typical wear, or more than 5 kilograms during typical wear. Although tension band assembly 45 is shown and described to be configured to pull the wearer's legs toward each other, the tension band assembly may alternatively be configured to pull the wearer's legs away from each other (i.e., outward). For examples, the front and/or rear straps of the tension band assembly may be spaced and/or positioned to pull the wearer's legs away from each other.

B. SECOND ILLUSTRATIVE TENSION BAND ASSEMBLY

Figure 4:
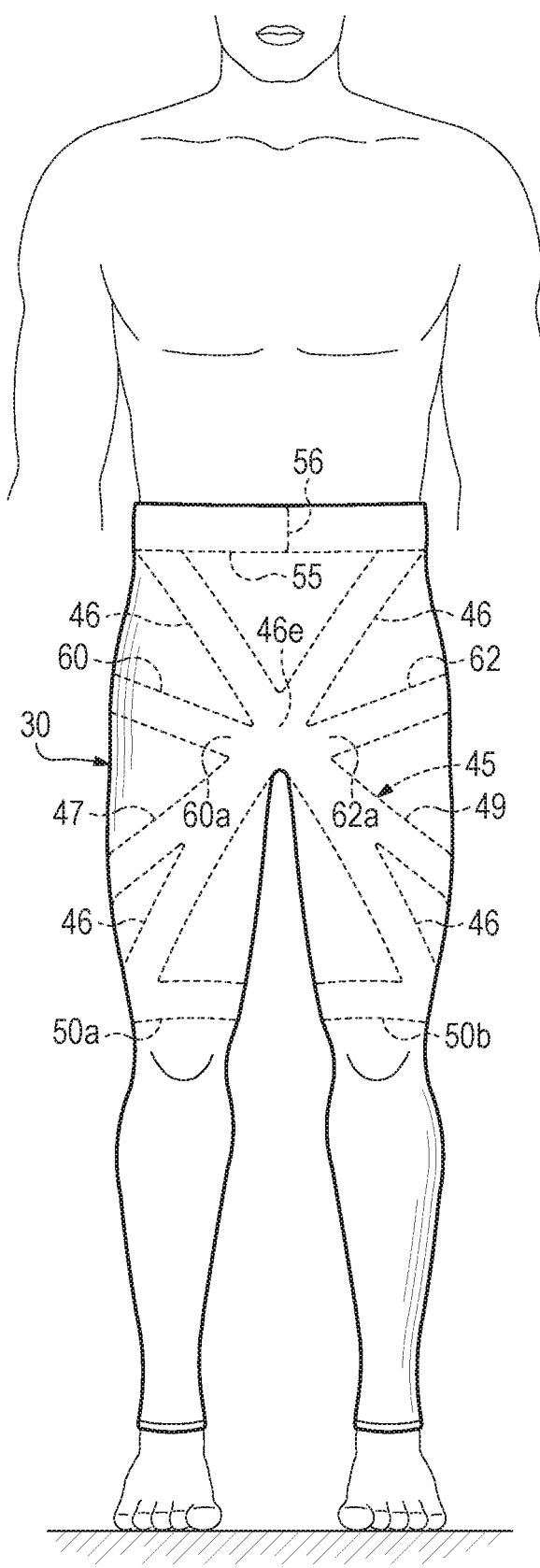
FIG. 4 is a front view of a second illustrative example of a resistance garment.
Figure 5:
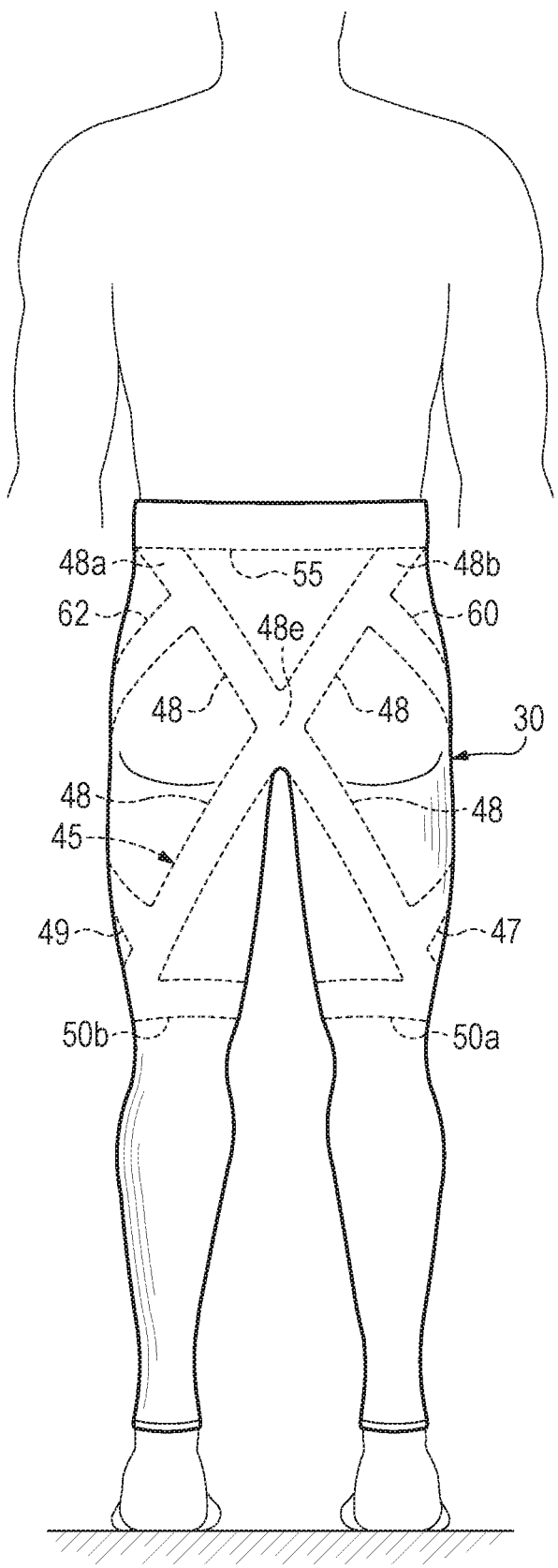
FIG. 5 is a back view of the resistance garment of FIG. 4.
Figure 6:
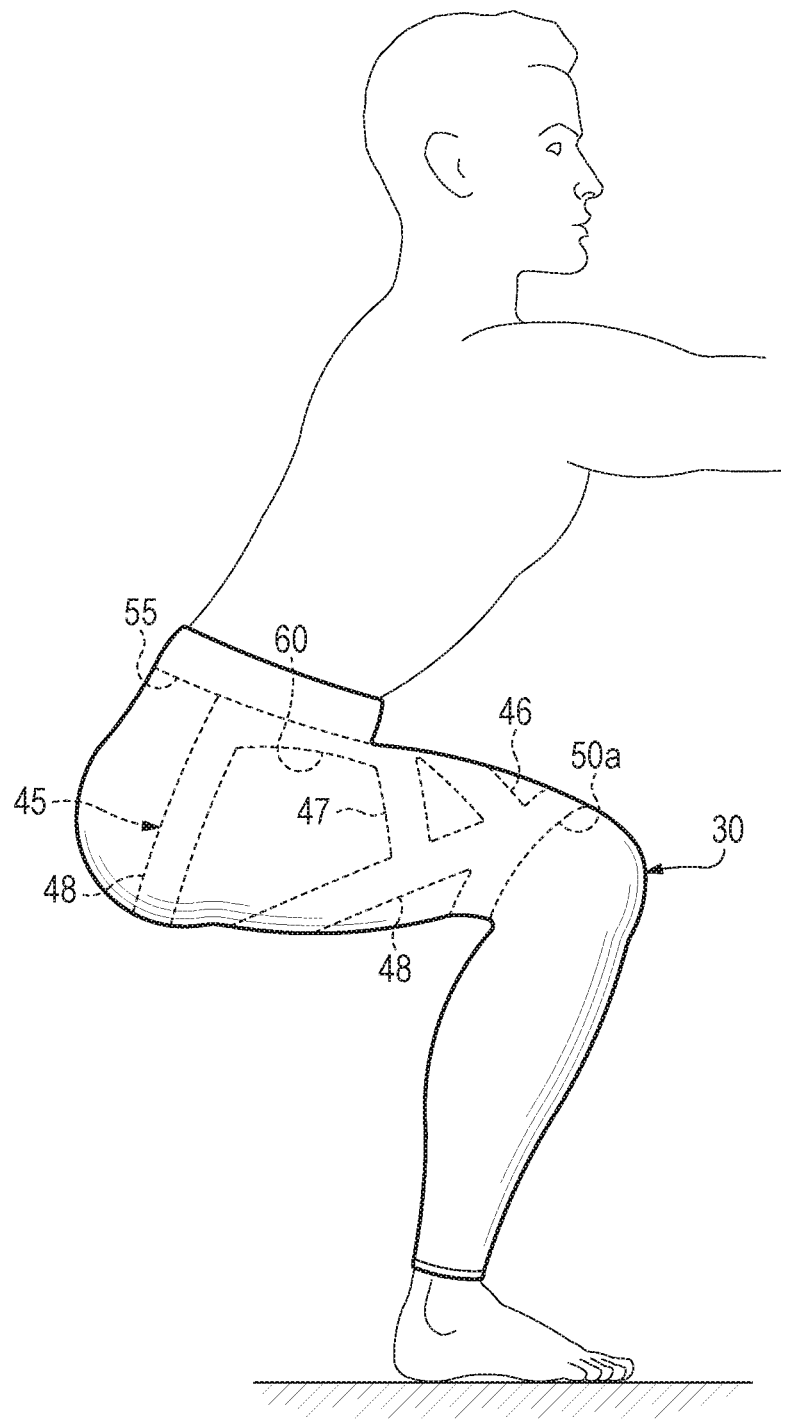
FIG. 6 is a side view of the resistance garment of FIG. 4, shown with the wearer performing a squat.

FIGS. 4-6 depict a second illustrative embodiment of tension band assembly 45. Aspects of the second illustrative embodiment may be combined with the embodiments described in other sections. In this embodiment, tension band assembly 45 further includes a third bridge strap 60 and a fourth bridge strap 62. Third bridge strap 60 includes opposed thirteenth end 60a and fourteenth end 60b, while fourth bridge strap 62 includes opposed fifteenth end 62a and sixteenth end 62b. The third and fourth bridge straps may connect any suitable portions of the front and rear straps. In the example shown in FIGS. 4-6, thirteenth end 60a is attached to, or formed with, front central portion 46a of the front straps, while fourteenth end 60 is attached to, or formed with, a portion of rear straps 48 between sixth end 48b and rear central portion 48e. Additionally, fifteenth end 62a is attached to, or formed with, front central portion 46a of the front straps, while sixteenth end 62b is attached to, or formed with, a portion of rear straps 48 between fifth end 48a and rear central portion 48e. Compared to embodiments omitting the third and fourth bridge straps, embodiments including the third and fourth bridge straps have a more even distribution of force over the wearer's legs, which may increase the comfort of the wearer.

FIG. 6 is a side view of resistance tights 30 including the second illustrative embodiment of tension band assembly 45. Third bridge strap 60 can be seen in FIG. 6 extending across the wearer's thigh to meet front strap 46. Front strap 46 ends at rear strap 48 at outer side 42a of leg portion 40a. In other embodiments, front strap 46 ends at knee band 50a (see FIG. 3), or a portion of front strap 46 ends at knee band 50a and a portion of front strap 46 ends at rear strap 48.

C. THIRD ILLUSTRATIVE TENSION BAND ASSEMBLY

Figure 7:
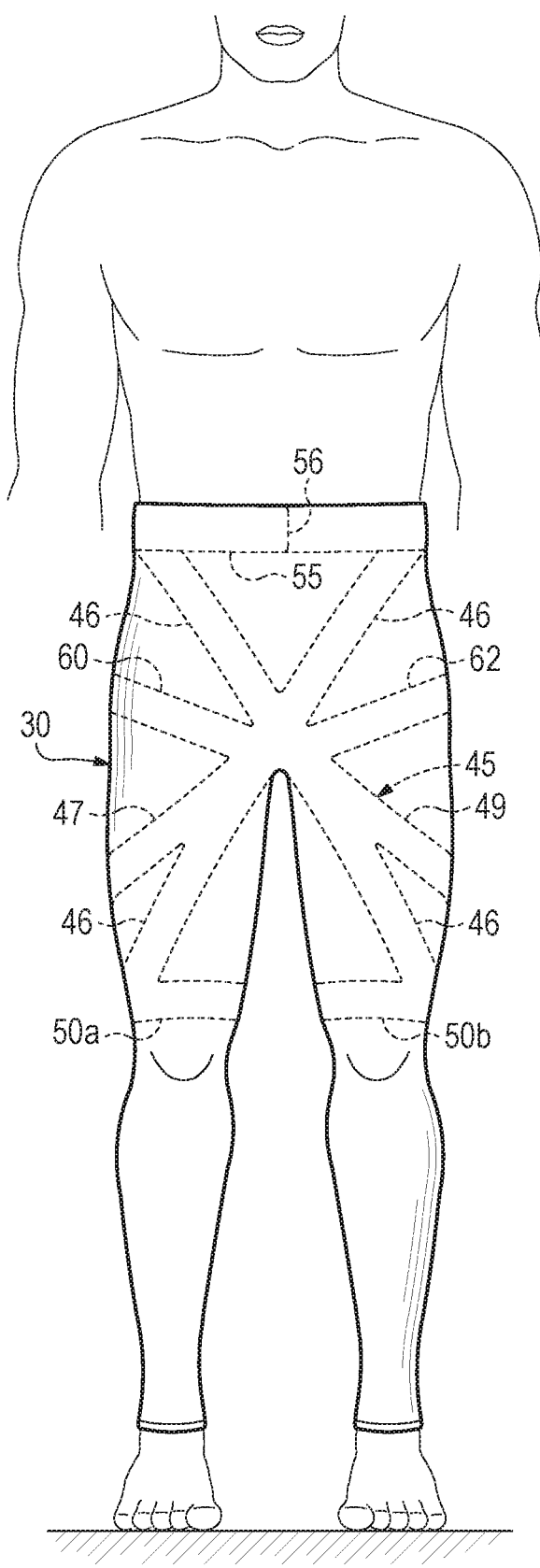
FIG. 7 is a front view of a third illustrative example of a resistance garment.
Figure 8:
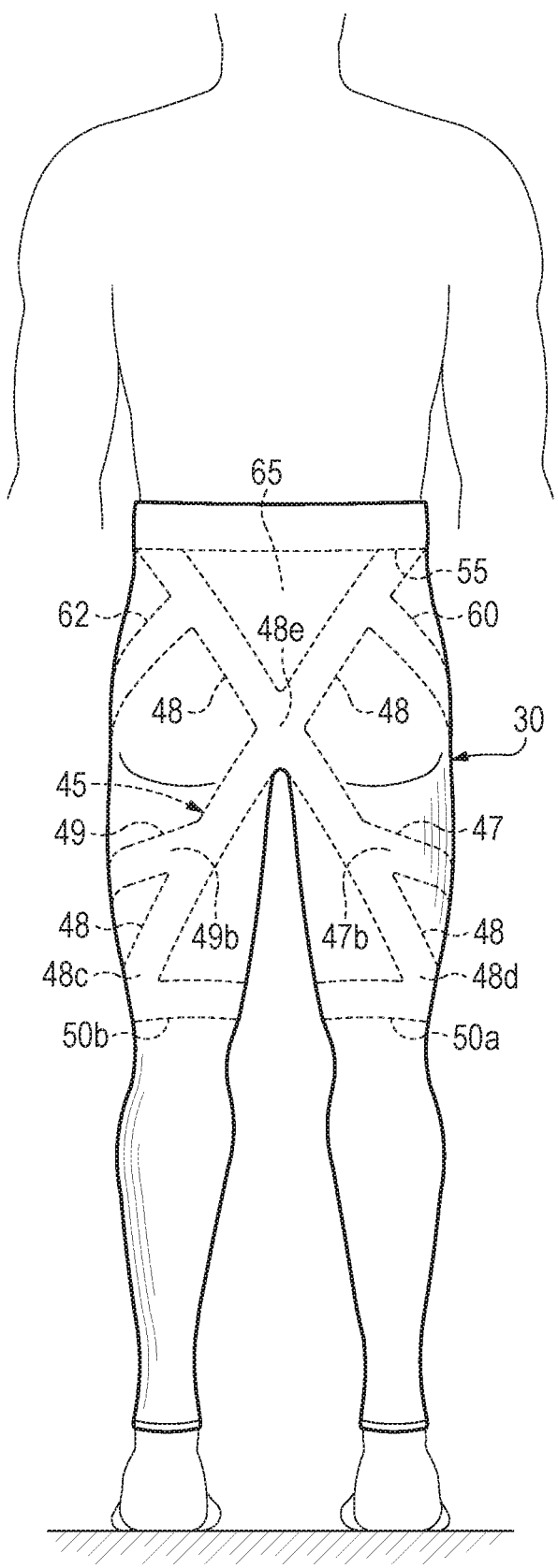
FIG. 8 is a back view of the resistance garment of FIG. 7.
Figure 9:
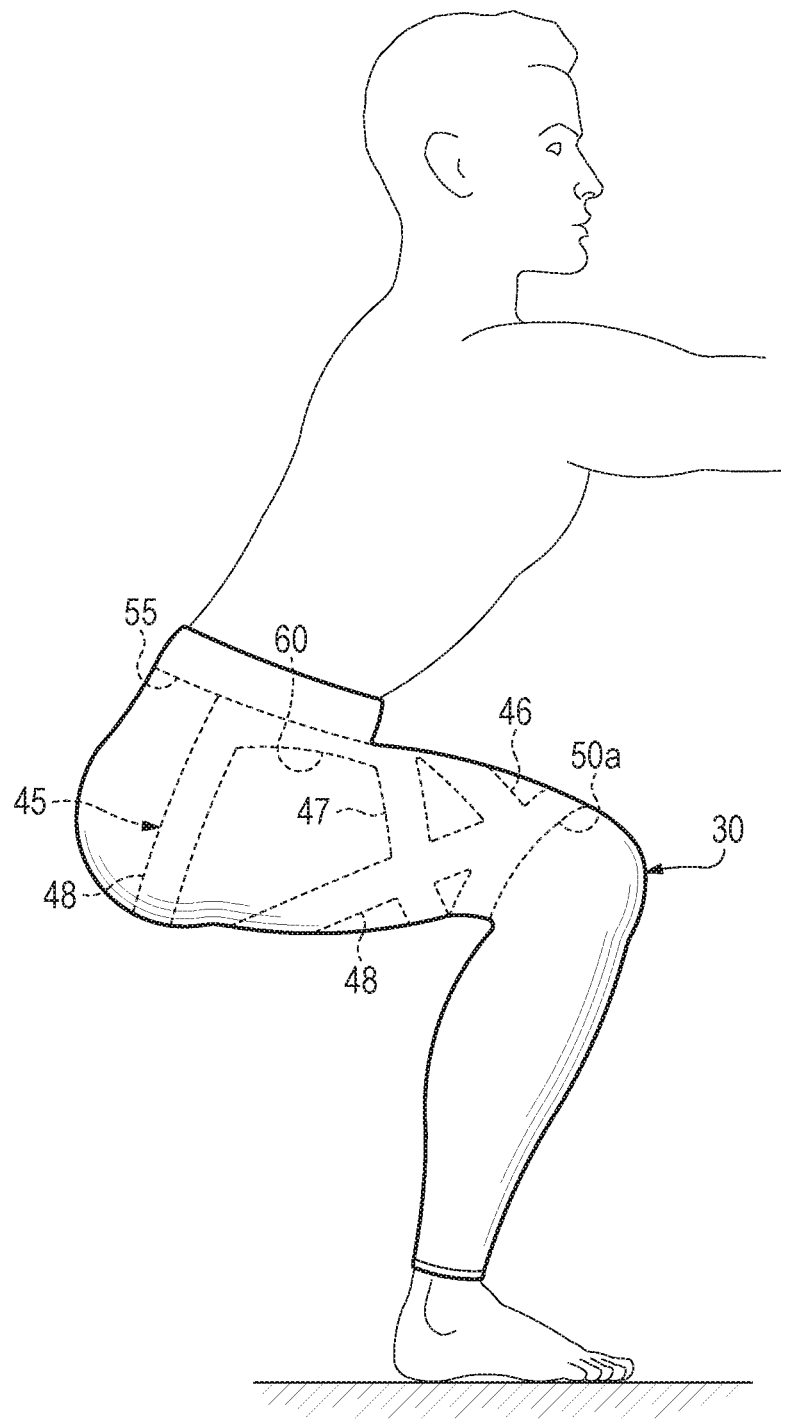
FIG. 9 is a side view of the resistance garment of FIG. 7, shown with the wearer performing a squat.

FIGS. 7-9 depict a third illustrative embodiment of tension band assembly 45. Aspects of the third illustrative embodiment may be combined with the embodiments described in other sections. In this embodiment, tenth end 47b of first bridge strap 47 is attached to, or formed with, a portion of rear straps 48 between rear central portion 48e and eighth end 48d (instead of being attached to, or formed with, eighth end 48d of the rear straps and/or the rear portion of first knee band 50a). Additionally, twelfth end 49b of second bridge strap 49 is attached to, or formed with, a portion of rear straps 48 between rear central portion 483 and seventh end 48c (instead of being attached to, or formed with, seventh end 48c of the rear straps and/or the rear portion of second knee band 50b). The example shown in FIGS. 7-9 distributes the tension applied by the rear straps over a greater portion of the wearer's legs, leading to increased comfort and reduced likelihood of injury.

As shown in FIG. 8, tension band assembly 45 may also include a tension panel 65 connecting upper portions of rear straps 48 and belt 55. Tension panel 65 is a fabric panel with a high degree of tension. The strong tension of tension panel 65 helps to retain rear straps 48 in a desired position across the wearer's gluteal muscles. Tension panel 65 may be formed by a fabric or other material that stretches by a relatively small amount when the wearer moves, such that the tension panel prevents undesirable displacement of rear straps 48 or other components of tension band assembly 45.

D. ADDITIONAL ILLUSTRATIVE EMBODIMENTS

Resistance tights 30 may include additional components useful for athletic activities. For example, resistance tights 30 may include hardened or cushioned panels at the wearer's shins to function as shin guards. Additionally, or alternatively, resistance tights 30 may include knee pads configured to protect the kneecaps of the wearer. In some embodiments, resistance tights 30 include padding typical of cycling shorts, configured to sit between the wearer's body and the saddle of a bicycle. Knee bands 50a, 50b and/or belt 55 may include braces configured to support the wearer's knees or back, respectively, to prevent injury or facilitate the healing of an injury. Knee bands 50a, 50b, belt 55, and/or other portions of resistance tights 30 may include heating or cooling elements. Reflective or illuminating elements may be included on any portion of resistance tights 30 to increase the visibility of the wearer. Resistance tights 30 may include one or more pockets.

In some embodiments, tension band assembly 45 of resistance tights 30 is configured to provide a high resistance to the wearer's movement, such that the effort required by the wearer to perform everyday activities while wearing the tights is significantly greater than the effort required to perform those activities without the tights. The resistance of tension band assembly 45 may be high enough in this case to make wearing resistance tights 30 during everyday activities impractical. These embodiments may be worn by athletes during training or warm-up exercises for athletic activities such as weight lifting, track and field, football, and others.

In some embodiments, resistance tights 30 serve as hosiery and may not be opaque. For example, resistance tights 30 may be hose with a relatively low denier. In such embodiments, resistance tights 30 may be worn underneath other garments, such as pants or a skirt. Resistance tights 30 may be designed as shapewear, including panels or other components configured to shape or compress a portion of the wearer's body. The fabric of resistance tights 30 may be colored to resemble the color of a wearer's skin to reduce the visibility of the tights when they are worn underneath another garment. The fabric of resistance tights 30 may be configured to be slippery or to reduce static electricity so as not to interfere with a skirt or dress worn over the tights.

The length of resistance tights 30 may be chosen such that the tights end at a wearer's thighs, knees, calves, or ankles. Knee bands 50a, 50b may be disposed at the wearer's knees, or above the wearer's knees, or below the wearer's knees. Leg portions 40a, 40b may extend beyond knee bands 50a, 50b. In embodiments in which leg portions 40a, 40b extend beyond knee bands 50a, 50b, resistance tights 30 may include elastic bands, cuffs, stirrups, or socks or other foot-covering portions at the ends of the leg portions to hold the leg portions in place. Resistance tights 30 may also extend above belt 55, including suspenders, bibs, and/or a shirt. In some embodiments, resistance tights 30 include only tension band assembly 45, with no fabric between the bands of the tension band assembly.

In some embodiments, front straps 46; rear straps 48; and/or other components of tension band assembly 45 include buckles, ratchets, or other mechanisms configured to selectively adjust or remove the tension provided by the straps. A wearer could use the tension-adjusting mechanism if they become tired, engage in an activity where the tension is unhelpful, or wish to alternate periods of gluteal activation with periods of rest (for example, as part of a physical therapy routine).

Although the above resistance garment is shown in the form of resistance tights 30 that cover a wearer's lower body portion and/or legs, the resistance garments of the present disclosure includes garments that additionally, or alternatively, cover one or more other portions of the wearer and that may additionally, or alternatively, facilitate and/or activate other muscles or muscle groups of the wearer. For example, the resistance garment may be in the form of a shirt that covers a wearer's upper body portion and with a tension band assembly that provides one or more forces that tend to move one or more portions of the wearer toward and/or away from each other (e.g., shoulders, arms, etc.). The front and/or rear straps may be spaced and/or positioned to move one or more portions of the wearer toward and/or away from each other. In some embodiments, the resistance garment may be in the form of a full body suit that facilitates and/or activates several muscle groups of the wearer, including or excluding the gluteal region.

E. SELECTED EMBODIMENTS AND CLAIM CONCEPTS

This section describes additional aspects and features of resistance garments with tension bands, presented without limitation as a series of paragraphs, some or all of which may be alphanumerically designated for clarity and efficiency. Each of these paragraphs can be combined with one or more other paragraphs, and/or with disclosure from elsewhere in this application, in any suitable manner. Some of the paragraphs below may expressly refer to and further limit other paragraphs, providing without limitation examples of some of the suitable combinations.

A0. A resistance garment comprising:
  a body portion configured to cover the pelvis of a wearer;
  first and second leg portions extending from the body portion, each configured to cover a leg of the wearer; and
  a system of elastic tension bands configured to apply a force tending to draw the legs of the wearer toward each other.

A1. The resistance garment of A0, wherein the system of elastic tension bands is further configured to apply a force tending to draw the legs of the wearer toward the torso of the wearer.

A2. The resistance garment of any one of paragraphs A0 through A1, wherein the system of elastic tension bands comprises:
  a first elastic front strap extending from a first side of the body portion proximate the first leg portion across a front side of the garment to an outer portion of the second leg portion;
  a second elastic front strap extending from a second side of the body portion proximate the second leg portion across a front side of the garment to an outer portion of the first leg portion.

A3. The resistance garment of A2, wherein the first and second elastic front straps are forked adjacent the outer portions of the first and second leg portions, such that the first and second elastic front straps apply tension to the legs of the wearer at two or more points.

A4. The resistance garment of any one of paragraphs A2 through A3, wherein the system of elastic tension bands comprises:
  a first elastic rear strap extending from a first side of the body portion proximate the first leg portion across a back side of the garment to an outer portion of the second leg portion;
  a second elastic rear strap extending from a second side of the body portion proximate the second leg portion across a back side of the garment to an outer portion of the first leg portion.

A5. The resistance garment of A4, wherein a tension of the first and second elastic rear straps is less than a tension of the first and second elastic front straps.

A6. The resistance garment of any one of paragraphs A4 through A5, wherein the first and second elastic rear straps are forked at the first and second leg portions, such that the first and second elastic rear straps apply tension to the legs of the wearer at two or more points.

A7. The resistance garment of any one of paragraphs A4 through A6, further comprising a tension panel adjacent upper portions of the first and second elastic rear straps, wherein the tension panel is configured to reduce movement of the elastic rear straps on the body of the wearer.

A8. The resistance garment of any one of paragraphs A4 through A7, further comprising first and second elastic middle straps extending from second and first elastic front straps across outer portions of the leg portions to first and second elastic rear straps.

A9. The resistance garment of any one of paragraphs A0 through A8, further comprising a tightening belt adjacent the body portion configured to embrace the torso of the wearer with a tightness selectable by the wearer.

A10. The resistance garment of any one of paragraphs A0 through A9, further comprising first and second elastic knee bands disposed in first and second leg portions adjacent the knees of the wearer.

Advantages, Features, Benefits

The different embodiments and examples of the resistance garment described herein provide several advantages over known solutions for facilitating gluteal activation and/or reducing gluteal amnesia. For example, illustrative embodiments and examples described herein allow a user to increase gluteal activation without wearing a knee band around both knees, which tends to impede movement and look unacceptable in many settings.

Additionally, and among other benefits, illustrative embodiments and examples described herein allow a single garment that provides both a tension force tending to move the wearer's knees together and a tension force tending to move the wearer's torso closer to their thighs.

Additionally, and among other benefits, illustrative embodiments and examples described herein allow a wearer to reduce or eliminate gluteal amnesia.

Additionally, and among other benefits, illustrative embodiments and examples described herein allow a wearer to increase gluteal engagement during physical training or sports activities, even if the wearer does not suffer from gluteal amnesia.

No known system or device can perform these functions. However, not all embodiments and examples described herein provide the same advantages or the same degree of advantage.

CONCLUSION

The disclosure set forth above may encompass multiple distinct examples with independent utility. Although each of these examples has been disclosed in its preferred form(s), the specific embodiments thereof as disclosed and illustrated herein are not to be considered in a limiting sense, because numerous variations are possible. The subject matter of the example(s) includes all novel and nonobvious combinations and subcombinations of the various elements, features, functions, and/or properties disclosed herein.

Certain combinations and subcombinations regarded as novel and nonobvious are particularly pointed out throughout this disclosure. Other combinations and subcombinations of features, functions, elements, and/or properties may be claimed, with or without variation in scope, in applications claiming priority from this or a related application.

Explicit reference is hereby made to all examples, embodiments, inventions, labels, terms, descriptions, and illustrative measurements shown in the drawings and/or in any included appendices, whether or not described further herein. To the extent that section headings are used within this disclosure, such headings are for organizational purposes only.

What is claimed is:

1. A resistance garment, comprising:
   a body portion configured to cover the pelvis of a wearer;
   first and second leg portions extending from the body portion, each sized to cover at least a portion of a thigh of the wearer; and
   an elastic strap assembly secured to the body portion and the first and second leg portions, the elastic strap assembly configured to apply (1) a first force at the wearer's hip that urges the thighs of the wearer toward the wearer's torso and (2) a second force at the wearer's thighs that urges the thighs of the wearer toward each other, the elastic band assembly including:
      a belt sized to extend around the waist of the wearer, the belt having front and rear portions,
      first and second knee bands sized to extend around lower portions of the wearer's thighs at or above the wearer's knees, the first and second knee bands each having front and rear portions,
      front elastic straps in the form of an X-shape having a front central portion and first, second, third, and fourth ends, wherein the first and second ends are attached to, or formed with, the front portion of the belt, wherein the third end is attached to, or formed with, the front portion of the first knee band, and wherein the fourth end is attached to, or formed with, the front portion of the second knee band, and
      rear elastic straps in the form of an X-shape having a rear central portion and fifth, sixth, seventh, and eighth ends, wherein the fifth and sixth ends are attached to, or formed with, the rear portion of the belt, wherein the seventh end is attached to, or formed with, the rear portion of the second knee band, and wherein the eighth end is attached to, or formed with, the rear portion of the first knee band,
   wherein the elastic strap assembly further includes:
      a first bridge elastic strap having opposed ninth and tenth ends, wherein the ninth end is attached to, or formed with, a portion of the front elastic straps between the front central portion and the third end, and wherein the tenth end is attached to, or formed with, the eighth end of the rear elastic straps; and
      a second bridge elastic strap having opposed eleventh and twelfth ends, wherein the eleventh end is attached to, or formed with, a portion of the front elastic straps between the front central portion and the fourth end, and wherein the twelfth end is attached to, or formed with, the seventh end of the rear elastic straps.

2. The resistance garment of claim 1, wherein the ninth and eleventh ends also are attached to, or formed with, opposed ends of the front central portion.

3. The resistance garment of claim 1, wherein the tenth end is also attached to, or formed with, the rear portion of the first knee band, and wherein the twelfth end is also attached to, or formed with, the rear portion of the second knee band.

4. The resistance garment of claim 1, wherein the elastic strap assembly further includes:
   a third bridge elastic strap having opposed thirteenth and fourteenth ends, wherein the thirteenth end is attached to, or formed with, the front central portion, and wherein the fourteenth end is attached to, or formed with, a portion of the rear elastic straps between the sixth end and the rear central portion; and
   a fourth bridge elastic strap having opposed fifteenth and sixteenth ends, wherein the fifteenth end is attached to, or formed with, the front central portion, and wherein the sixteenth end is attached to, or formed with, a portion of the rear elastic straps between the fifth end and the rear central portion.

5. The resistance garment of claim 1, wherein the elastic strap assembly further includes:
   a third bridge elastic strap having opposed thirteenth and fourteenth ends, wherein the thirteenth end is attached to, or formed with, the front central portion, and wherein the fourteenth end is attached to, or formed with, a portion of the rear elastic straps between the sixth end and the rear central portion; and
   a fourth bridge elastic strap having opposed fifteenth and sixteenth ends, wherein the fifteenth end is attached to, or formed with, the front central portion, and wherein the sixteenth end is attached to, or formed with, a portion of the rear elastic straps between the fifth end and the rear central portion.

6. The resistance garment of claim 1, wherein the body portion and the first and second leg portions include inner and outer layers, and wherein the elastic strap assembly is disposed between the inner and outer layers.

7. The resistance garment of claim 1, wherein the first and second leg portions are each sized to cover a thigh and at least a portion of a knee of the wearer.

8. The resistance garment of claim 1, wherein the first and second leg portions are each sized to cover a thigh, a knee, and at least a portion of a leg of the wearer.

9. The resistance garment of claim 1, wherein the first and second leg portions are each sized to cover a thigh, a knee, and a leg of the wearer.

10. The resistance garment of claim 1, wherein the belt includes an elastic band sized to extend around the waist of the wearer.

11. The resistance garment of claim 1, wherein the belt includes a strap sized to extend around the waist of the wearer, the strap having first and second end portions, wherein the second end portion of the belt includes a buckle configured to receive the first end portion of the strap to allow the wearer to adjust the circumference of the strap.

12. The resistance garment of claim 11, wherein the buckle includes two rings configured to receive the first end portion of the strap.

13. The resistance garment of claim 11, wherein the belt includes means for adjusting the circumference of the strap.

14. The resistance garment of claim 1, wherein the body portion and the first and second leg portions include at least one skintight layer.

15. A resistance garment, comprising:
   a body portion configured to cover the pelvis of a wearer;
   first and second leg portions extending from the body portion, each sized to cover at least a portion of a thigh of the wearer; and
   an elastic strap assembly secured to the body portion and the first and second leg portions, the elastic strap assembly configured to apply (1) a first force at the wearer's hip that urges the thighs of the wearer toward the wearer's torso and (2) a second force at the wearer's thighs that urges the thighs of the wearer toward each other, the elastic band assembly including:
      a belt sized to extend around the waist of the wearer, the belt having front and rear portions,
      first and second knee bands sized to extend around lower portions of the wearer's thighs at or above the wearer's knees, the first and second knee bands each having front and rear portions, front elastic straps in the form of an X-shape having a front central portion and first, second, third, and fourth ends, wherein the first and second ends are attached to, or formed with, the front portion of the belt, wherein the third end is attached to, or formed with, the front portion of the first knee band, and wherein the fourth end is attached to, or formed with, the front portion of the second knee band, rear elastic straps in the form of an X-shape having a rear central portion and fifth, sixth, seventh, and eighth ends, wherein the fifth and sixth ends are attached to, or formed with, the rear portion of the belt, wherein the seventh end is attached to, or formed with, the rear portion of the second knee band, and wherein the eighth end is attached to, or formed with, the rear portion of the first knee band, a first bridge elastic strap having opposed ninth and tenth ends, wherein the ninth end is attached to, or formed with, the front central portion and a portion of the front elastic straps between the front central portion and the third end, and wherein the tenth end is attached to, or formed with, one of (i) the eighth end of the rear elastic straps and the rear portion of the first knee band or (ii) a portion of the rear elastic straps between the rear central portion and the eighth end, and a second bridge elastic strap having opposed eleventh and twelfth ends, wherein the eleventh end is attached to, or formed with, the front central portion and a portion of the front elastic straps between the front central portion and the fourth end, and wherein the twelfth end is attached to, or formed with, one of (a) the seventh end of the rear elastic straps and rear portion of the second knee band or (b) a portion of the rear elastic straps between the rear central portion and the seventh end.

16. The resistance garment of claim 15, wherein the elastic strap assembly further includes:

a third bridge elastic strap having opposed thirteenth and fourteenth ends, wherein the thirteenth end is attached to, or formed with, the front central portion, and wherein the fourteenth end is attached to, or formed with, a portion of the rear elastic straps between the sixth end and the rear central portion; and a fourth bridge elastic strap having opposed fifteenth and sixteenth ends, wherein the fifteenth end is attached to, or formed with, the front central portion, and wherein the sixteenth end is attached to, or formed with, a portion of the rear elastic straps between the fifth end and the rear central portion.

17. A resistance garment, comprising:

a body portion configured to cover the pelvis of a wearer;

first and second leg portions extending from the body portion, each sized to cover at least a portion of a thigh of the wearer; and an elastic strap assembly secured to the body portion and the first and second leg portions, the elastic strap assembly configured to apply (1) a first force at the wearer's hip that urges the thighs of the wearer toward the wearer's torso and (2) a second force at the wearer's thighs that urges the thighs of the wearer toward each other, the elastic band assembly including:

a belt sized to extend around the waist of the wearer, the belt having front and rear portions, first and second knee bands sized to extend around lower portions of the wearer's thighs at or above the wearer's knees, the first and second knee bands each having front and rear portions, front elastic straps in the form of an X-shape having a front central portion and first, second, third, and fourth ends, wherein the first and second ends are attached to, or formed with, the front portion of the belt, wherein the third end is attached to, or formed with, the front portion of the first knee band, and wherein the fourth end is attached to, or formed with, the front portion of the second knee band, and rear elastic straps in the form of an X-shape having a rear central portion and fifth, sixth, seventh, and eighth ends, wherein the fifth and sixth ends are attached to, or formed with, the rear portion of the belt, wherein the seventh end is attached to, or formed with, the rear portion of the second knee band, and wherein the eighth end is attached to, or formed with, the rear portion of the first knee band, wherein the elastic strap assembly further includes:

a first bridge elastic strap having opposed ninth and tenth ends, wherein the ninth end is attached to, or formed with, a portion of the front elastic straps between the front central portion and the third end, and wherein the tenth end is attached to, or formed with, a portion of the rear elastic straps between the rear central portion and the eighth end; and a second bridge elastic strap having opposed eleventh and twelfth ends, wherein the eleventh end is attached to, or formed with, a portion of the front elastic straps between the front central portion and the fourth end, and wherein the twelfth end is attached to, or formed with, a portion of the rear elastic straps between the rear central portion and the seventh end.

\* \* \* \* \*